(12) United States Patent
Arnaud et al.

(10) Patent No.: US 6,280,714 B1
(45) Date of Patent: Aug. 28, 2001

(54) LIP CARE COMPOSITION CONTAINING ACEXAMIC ACID, AND USES THEREOF

(75) Inventors: Pascal Arnaud, L'Hay les Roses; Lionel Breton, Versailles, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/231,173

(22) Filed: Jan. 13, 1999

(30) Foreign Application Priority Data

Jan. 13, 1998 (FR) ................................................ 98 00247
Mar. 5, 1998 (FR) ................................................ 98 02717

(51) Int. Cl.$^7$ ............................... A61K 6/00; A61K 7/00; A61K 7/025
(52) U.S. Cl. .............................. 424/64; 424/401
(58) Field of Search ........................ 424/64, 401

(56) References Cited

U.S. PATENT DOCUMENTS 5,741,518 * 4/1998 Ribier et al. .................. 424/450
6,033,650 * 3/2000 Calello et al. .................. 424/64

FOREIGN PATENT DOCUMENTS

| 0 214 357 | 3/1987 | (EP) . |
| 0 465 313 | 1/1992 | (EP) . |
| 0 667 146 | 8/1995 | (EP) . |
| 2 730 931 | 8/1996 | (FR) . |
| 4-360810 | 12/1992 | (JP) . |

OTHER PUBLICATIONS

Royal Pharmaceutical Society, "Martindale The Extra Pharmacopoeia", London, 1995, p. 1668, col. 2.
A. Korolkovas, "Essentials of Medicinal Chemistry. Second Edition", Wiley–Interscience Publication, New York, 1988, p. 560.
English language Derwent Abstract of EP 0 465 313.
English language Derwent Abstract of EP 0 667 146.
English language Derwent Abstract of FR 2 730 931.
English language Derwent Abstract of JP 4–360810.

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, LLP

(57) ABSTRACT

A lip care composition, in particular an anhydrous composition, containing, as physiologically acceptable active care agent, acexamic acid, preferably dissolved or dispersed in a fatty phase. This composition can be in the form of a stick, in particular a stick of lipstick or of lip balm, to protect the lips in particular against bad weather and thus to prevent them from drying out and/or from cracking and chapping.

30 Claims, No Drawings

LIP CARE COMPOSITION CONTAINING ACEXAMIC ACID, AND USES THEREOF

The present invention relates to a care and/or treatment composition for human lips, containing acexamic acid [also known as acetamidocaproic acid or 6-(acetylamino) hexanoic acid]. This composition can be used in the cosmetics or dermatological field. Preferably, this composition is in the form of an optionally coloured, homogeneous, anhydrous stick, cream or gel containing this active agent. In particular, this composition can avoid drying-out, the formation of cracks or chapping, and can be useful for the treatment of existing cracks and chapping. It also makes the lips supple and soft, and can be used to resolve oedemas and suppress pain in the lips.

To protect the lips against drying out, lip balms in stick form are generally used. These balms contain treating oils, generally of plant origin such as triglycerides (see in this respect document JP-A-04,360,810). Unfortunately, even in large amounts, these oils do not treat the lips sufficiently, especially when they are swollen or cracked or chapped. In addition, the larger the amount of these oils, the greasier the feel of the balm, thus giving the lips an unaesthetic appearance and giving mediocre cosmetic properties in terms of application, i.e., greasy or heavy. It is thus desirable to limit this greasy appearance in a make-up product for the lips. Moreover, it is difficult at the present time to obtain lip products, with treating properties, which contain little or no oil of plant origin.

The subject of the invention is, precisely, a care and/or treatment composition for the lips which overcomes these drawbacks. Surprisingly, the inventors have found that the use of acexamic acid in a care or make-up base for the lips, of any type, allows them to be treated, prevents them from drying out and prevents the formation of cracking and/or chapping. In particular, the composition allows the lips to be made up and/or protected aesthetically while at the same time treating them, irrespective of the fatty phase of the said composition.

The invention applies not only to care and/or treatment products for the lips, but also to make-up products for the lips which have care and/or treating properties.

More precisely, the invention relates to a care or make-up composition for the lips containing acexamic acid, as physiologically acceptable active care agent, and a fatty phase containing this active agent, the fatty phase containing at least one oil selected from hydrocarbon-based oils having at least four carbon atoms, silicone oils, and fluorinated oils.

The acexamic acid can be used in particular in a proportion of from 0.05 to 10%, and better still from 0.1 to 5%, of the total weight of the composition. It can be in free form or in the form of a salt, in particular in the form of a zinc salt.

Preferably, the acexamic acid is in the form of a powder, which allows it to be incorporated easily into the fatty phase, in soluble or dispersed form, which is not always the case for an active agent in liquid form, which can have problems with emulsion stabilization and can require sophisticated apparatus to prepare certain emulsions thereof.

This composition can be used just as it is or it can be incorporated into a more complex composition. In particular, it does not feel sticky or greasy and is soft to apply, while at the same time treating the lips in a satisfactory manner.

For example, the composition of the invention can be in paste, solid, cream or even liquid form. It can be an oil-in-water or water-in-oil emulsion, a solid or supple anhydrous gel or a liquid oily phase. Preferably, it is in the form of an anhydrous solid composition and more especially in the form of a stick.

Preferably, the composition contains a certain amount of hydroxylated oil to dissolve the acexamic acid or to disperse it correctly. Advantageously, these oils have a hydroxyl group index $\geq 50$ and <750. They preferably have at least four carbon atoms. More preferably, they are hydrocarbon-based oils.

As hydroxylated oils which can be used in the invention, mention may be made in particular of:

synthetic esters and ethers such as $C_{12}$–$C_{13}$ alkyl lactate, isostearyl lactate, octyl hydroxystearate, octyidodecyl hydroxystearate, diisostearyl malate, propylene glycol monoisostearate, polyglyceryl-3 diisostearate and PPG-10 butanediol;

liquid triglycerides such as castor oil;

$C_{12}$ to $C_{26}$ fatty alcohols such as octyidodecanol, 2-hexyldecanol, 2-undecylpentadecanol or oleyl alcohol;

mixtures thereof.

It is, however, possible to use non-hydroxylated oils which may or may not be combined with the above hydroxylated oils. These non-hydroxylated oils can be hydrocarbon-based oils, silicone oils and/or fluoro oils. As hydrocarbon-based non-hydroxylated oil which can be used in the invention, mention may be made of:

liquid triglycerides of linear or branched, saturated or unsaturated fatty acids of 4 to 10 carbon atoms, which are liquid at room temperature, such as heptanoic or octanoic acid triglyceride, sunflower oil, corn oil, wheatgerm oil, soybean oil, marrow oil, grapeseed oil, blackcurrant seed oil, evening primrose oil, millet oil, barley oil, quinoa oil, olive oil, rye oil, safflower oil, candlenut oil, passion flower oil, musk rose oil, sesame oil, hazelnut oil, apricot oil, macadamia oil, sweet almond oil, avocado oil, cottonseed oil, lucerne oil, poppy oil or pumpkin oil, caprylic/capric acid triglycerides such as those sold by the company Stearineries Dubois or those sold under the names Miglyol 810, 812 and 818 by the company Dynamit Nobel, jojoba oil or karite butter;

synthetic esters and ethers, in particular of fatty acids, such as oils of formula $R_3COOR_4$ in which $R_3$ represents a $C_7$ to $C_{29}$ higher fatty acid residue and $R_4$ represents a $C_3$ to $C_{30}$ hydrocarbon-based chain, such as purcellin oil, isopropyl myristate, 2-ethylhexyl palmitate, 2-octyldodecyl stearate, octacosanyl stearate, 2-octyldodecyl erucate, isostearyl isostearate; triisocetyl citrate, fatty acid heptanoates, octanoates, decanoates or ricinoleates; polyol esters such as propylene glycol dioctanoate, neopentyl glycol diheptanoate, diethylene glycol diisononanoate; and pentaerythritol esters;

linear or branched hydrocarbons of synthetic or mineral origin, such as volatile or non-volatile liquid paraffins and their derivatives, petroleum jelly, polydecenes, hydrogenated polyisobutene such as parleam or perhydrosqualene;

mixtures thereof.

The silicone oils which can be used in the invention are, in particular, linear or cyclic, volatile or non-volatile polydimethylsiloxanes (PDMS) which are liquid or pasty at room temperature, the polydimethylsiloxanes containing alkyl, alkoxy or phenyl groups, pendant or at the end of the silicone chain, these groups containing from 2 to 24 carbon atoms, such as triphenylmethicones, diphenyidimethicones, phenyldimethicones, polymethylphenylsiloxanes, diphenylmethyldimethyltrisiloxanes and phenyltrimethylsiloxydiphenylsiloxanes. The silicone oils can, furthermore, be fluorinated.

The hydroxylated oils represent preferably from 0.2 to 99.95% of the total weight of the composition, more preferably from 1 to 80%. The non-hydroxylated oils preferably represent from 0 to 99.95% of the weight of the composition, and better still from 0 to 50%.

The composition of the invention can also comprise any ingredient usually used in the field concerned, such as water, preferably in an amount ranging from 0 to 95% of the total weight of the composition, water-soluble or liposoluble dyes, antioxidants, essential oils, preserving agents, fragrances, neutralizing agents, liposoluble polymers, in particular hydrocarbon-based polymers such as polyalkylenes or polyvinyl laurate, gelling agents for an aqueous phase, gelling agents for a liquid fatty phase, waxes, gums, surfactants, additional cosmetic or dermatological active agents such as, for example, emollients, moisturizers (for example glycerol), vitamins, liquid lanolin, essential fatty acids, lipophilic or hydrophilic sunscreens, and mixtures thereof. The composition according to the invention can also contain lipid vesicles of ionic and/or nonionic type. These ingredients (other than the water) can preferably be present in the composition in a proportion of from 0 to 20% of the total weight of the composition.

Needless to say, a person skilled in the art will take care to select the optional complementary ingredients and/or the amount thereof such that the advantageous properties of the composition according to the invention are not, or are not substantially, adversely affected by the addition envisaged.

The composition according to the invention is preferably and advantageously in an anhydrous thickened form. Thus, the invention relates more especially to a thickened, anhydrous make-up or care composition for the lips, containing at least one thickener chosen from gelling agents for a fatty phase, waxes and fillers, and mixtures thereof. The waxes can be hydrocarbon-based, fluoro and/or silicone waxes and can be of plant, mineral, animal and/or synthetic origin. Preferably, the waxes have a melting point of greater than 25° C. and better still greater than 45° C.

As gelling agents for a fatty phase, mention may be made of optionally modified clays such as hectorites modified with a $C_{10}$ to $C_{22}$ fatty acid ammonium chloride, such as hectorite modified with distearyldimethylammonium chloride; silica; partially or totally crosslinked elastomeric polyorganosiloxanes of three-dimensional structure, such as those sold under the names KSG6, KSG16 and KSG18 by Shin-Etsu, Trefil E-505C or Trefil E-506C by Dow Coming, Gransil SR-CYC, SR DMF10, SR-DC556, SR 5CYC gel, SR DMF 10 gel and SR DC 556 gel by Grant Industries, and SF 1204 and JK 113 by General Electric; galactomannans containing from one to six and better still from two to four hydroxyl groups per saccharide, substituted with a saturated or unsaturated alkyl chain, such as guar gum alkylated with $C_1$ to $C_6$, and better still $C_1$ to $C_3$, alkyl chains, and more particularly ethylated guar having a degree of substitution of from 2 to 3, such as the product sold by the company Aqualon under the name N-Hance-AG; gums, in particular silicone gums such as PDMSs having a viscosity >500,000 centistokes. These gelling agents are used, for example, at concentrations of from 0.2 to 15% of the total weight of the composition.

Representative waxes which can be used in the invention include hydrocarbon-based, silicone and/or fluoro waxes, optionally containing ester, hydroxyl or thiol functions. Examples which may be mentioned are lanolin, beeswax, camauba wax, candelilla wax, paraffin, lignite wax, microcrystalline wax, ceresin or ozokerite; synthetic waxes such as polyethylene waxes, silicone waxes, for instance alkyl- or alkoxydimethicone containing from 16 to 45 carbon atoms, and Fischer-Tropsch waxes, and mixtures thereof.

The nature and amount of the waxes depend on the desired mechanical and textural properties. As a guide, the composition can preferably contain from 0 to 50% by weight of waxes, relative to the total weight of the composition, and better still from 5 to 30%. These waxes are also structuring agents for the composition.

The composition according to the invention can be in the form of a dermatological or care composition for the lips or in the form of an antisun composition for the lips. In this case, it is preferably in uncoloured form, optionally containing cosmetic or dermatological active agents other than acexamic acid. It can then be used as a care base for the lips (lip balms for protecting the lips against the cold and/or the sun and/or the wind).

The composition of the invention can also be in the form of a coloured make-up product for the lips, such as a lipstick or a lip gloss, which has care or treating properties. Thus, another subject of the invention is a thickened anhydrous make-up composition for the lips containing acexamic acid as physiologically acceptable active care agent, and a fatty phase containing this active agent and a thickener.

Needless to say, the composition of the invention must be cosmetically or dermatologically acceptable, i.e. acceptably non-toxic, and must be capable of being applied to human lips.

The composition of the invention can advantageously comprise a particulate phase, which is generally present in a proportion of from 0 to 35% of the total weight of the composition, preferably from 0.5 to 25%, and which can comprise pigments and/or pearlescent agents and/or fillers usually used in cosmetic or dermatological compositions.

The term pigments should be understood to refer to white or coloured, inorganic or organic particles which are insoluble in the liquid fatty phase and are intended to colour and/or opacify the composition. The term fillers should be understood to refer to colourless or white, inorganic or synthetic, lamellar or non-lamellar particles. The term pearlescent agents should be understood to refer to iridescent particles, in particular those produced by certain molluscs in their shell or alternatively synthesized. These fillers and pearlescent agents serve in particular to modify the texture of the composition and in particular form part of the structuring agents capable of leading to a solid form.

The pigments can preferably be present in the composition in a proportion of from 0.05 to 25% of the weight of the final composition, and more preferably in a proportion of from 2 to 15%. As inorganic pigments which can be used in the invention, mention may be made of titanium oxide, zirconium oxide or cerium oxide, as well as zinc oxide, iron oxide, chromium oxide and ferric blue. Among the organic pigments which can be used in the invention, mention may be made of carbon black and barium, strontium, calcium (DC Red No. 7) and aluminium lakes.

The pearlescent agents can preferably be present in the composition in a proportion of from 0 to 20% of the total weight of the composition, more preferably in a content of about 1 to 15%. Among the pearlescent agents which can be used in the invention, mention may be made of mica coated with titanium oxide, with iron oxide, with natural pigment or with bismuth oxychloride, such as coloured titanium mica.

The fillers can preferably be present in a proportion of from 0 to 35% of the total weight of the composition, more preferably 0.5 to 15%. Mention may be made in particular of talc, mica, kaolin, Nylon (in particular Orgasol) powder, polyethylene powder, Teflon, starch, boron nitride, copolymer microspheres such as Expancel (Nobel Industrie), Polytrap (Dow Coming) and silicone resin microbeads (for example Tospearl from Toshiba).

The composition according to the invention can be manufactured by the known processes generally used in the cosmetics or dermatological field. In particular, it can be obtained by heating the various constituents to the highest melting point of the waxes, followed by casting the molten mixture in a mould (crucible or finger stall). It can also be obtained by extrusion as described in application EP-A-667,146, the disclosure of which is specifically incorporated by reference herein.

In order to ensure effective protection against UV radiation, it is advantageous to add one or more organic or inorganic, lipophilic or hydrophilic screening agents to the composition.

Another subject of the invention is a cosmetic care or treatment process for human lips, comprising the application of the composition as defined above to the lips, in particular dry, cracked or chapped lips.

Another subject of the invention is the use of acexamic acid in a cosmetic composition or for the manufacture of a dermatological composition to limit, or even prevent altogether, the drying-out and/or oedema of the lips, cracking and chapping, and/or to protect the lips against bad weather.

The invention is illustrated in greater detail in the examples which follow. The percentages are given on a weight basis.

EXAMPLE 1
Care Stick for the Lips

| | |
|---|---|
| Castor oil | 11.14% |
| Hydroxyoctacosanyl hydroxystearate | 3.74% |
| Octacosanyl stearate | 7.54% |
| Fragrance | 0.50% |
| Hectorite modified with distearyldimethyl-ammonium chloride | 0.66% |
| Acexamic acid | 0.30% |
| Vinyl polylaurate | 8.90% |
| Polyethylene wax (molecular weight 500) | 3.67% |
| Propylene glycol monoisostearate | qs 100% |

Preparation: The acexamic acid is predissolved in the castor oil at 100° C. The rest of the constituents except for the fragrance are then added and the mixture is melted at 100° C. After homogenization, the fragrance is introduced and the mixture is then cast in a mould which is suitable for obtaining a stick.

An anhydrous white stick with a pleasant texture, which slides well and applies well to the lips is obtained, this stick having treating properties on the lips and in particular providing protection against drying and cracking.

This balm was tested, by daily application for one week, by 30 women with dry lips and users of this type of product, and without changing their lip make-up habits.

The results below show a marked improvement in the condition of the lips at the end of the treatment.

69% of the women find that their lips are smoother, 49% of these women have softer lips and 31 % of these women have more supple lips, 20 out of the 30 women find the balm comfortable or very comfortable when applied and that it has a good texture and is easy to apply, although the balm is felt to be slightly greasy.

EXAMPLE 2
Lip Balm

| | |
|---|---|
| Carnauba wax | 12.75% |
| Castor oil | qs 100% |
| Acexamic acid | 0.25% |
| Oxypropylenated (5 propylene oxides) lanolin wax | 15.00% |

After melting the camauba and lanolin waxes at 100° C., the castor oil containing the acexamic acid is introduced and the resulting mixture is then mixed and poured into a suitable mould.

EXAMPLE 3
Lip Balm

| | |
|---|---|
| Polyethylene wax (MW 500) | 3.30% |
| Propylene glycol monoisostearate | qs 100% |
| Acexamic acid | 0.25% |
| Oxypropylenated (5 propylene oxides) lanolin wax | 15.00% |
| Octacosanyl stearate | 7.60% |
| Hydroxyoctacosanyl hydroxystearate (wax) | 4.20% |

This lip balm is soft and slippery.

EXAMPLE 4
Lip Balm

| | |
|---|---|
| Polyethylene wax (MW 500) | 3.30% |
| Propylene glycol monoisostearate | qs 100% |
| Acexamic acid | 0.25% |
| Oxypropylenated (5 propylene oxides) lanolin wax | 12.00% |
| Octacosanyl stearate | 7.60% |
| Hydroxyoctacosanyl hydroxystearate | 4.20% |
| Polybutene | 10.00% |

This balm is less slippery and slightly less greasy than that of Example 3.

EXAMPLE 5
Lipstick

| | |
|---|---|
| Polyethylene wax (MW 500) | 3.30% |
| Propylene glycol monoisostearate | qs 100% |
| Acexamic acid | 0.25% |
| Oxypropylenated (5 propylene oxides) lanolin wax | 8.00% |
| Octacosanyl stearate | 7.60% |
| Hydroxyoctacosanyl hydroxystearate | 4.20% |
| Polybutene | 10.00% |
| Pigments | 8.66% |
| Fragrance | 0.50% |

The pigments are a mixture of titanium oxide, black iron oxide and organic lakes.

Preparation: The pigments are ground in a mixture containing a fraction of propylene glycol monoisostearate, the lanolin wax and the polybutene. The other waxes are added and the mixture is melted at 100° C. After homogenization, the acexamic acid solution obtained at 100° C. in the rest of the propylene glycol monoisostearate is added. The fragrance is added and the mixture is then cast in a mould which is suitable for obtaining a stick.

EXAMPLE 6
Lipstick

| | |
|---|---|
| Polyethylene wax (MW 500) | 3.35% |
| Propylene glycol monoisostearate | qs 100% |
| Acexamic acid | 0.30% |
| Polyvinyl laurate | 8.00% |
| Octacosanyl stearate | 6.84% |
| Hydroxyoctacosanyl hydroxystearate | 3.40% |
| Castor oil | 10.00% |
| Quarternium-18 hectorite (bentone) | 1.20% |
| Pigments | 8.66% |
| Fragrance | 0.50% |

This lipstick is prepared as for the one in Example 5.

EXAMPLE 7
Lipstick

| | |
|---|---|
| Polyethylene wax (MW 500) | 12.00% |
| Liquid lanolin | 15.00% |
| Phenyltrimethicone (DC556 from Dow Corning) | 63.34% |
| Pigments | 8.66% |
| Acexamic acid | 1.00% |

Preparation: The pigments and the acexamic acid are ground in a mixture containing phenyltrimethicone and the liquid lanolin. The rest of the constituents are melted at 100° C. and are then added to the mixture. After homogenization, this mixture is cast in a suitable mould. The acexamic acid is dispersed in this lipstick.

What is claimed is:

1. A care or make-up composition for the lips comprising a fatty phase comprising acexamic acid as a physiologically acceptable active care agent and at least one oil selected from hydrocarbon-based oils having at least 4 carbon atoms, silicone oils, and fluorinated oils.

2. A composition according to claim 1, wherein the amount of said acexamic acid ranges from 0.05 to 10% of the total weight of the composition.

3. A composition according to claim 2, wherein the amount of said acexamic acid ranges from 0.1 to 5% of the total weight of the composition.

4. A composition according to claim 1 wherein said acexamic acid is in free form or in the form of a salt.

5. A composition according to claim 2 wherein said acexamic acid is in free form or in the form of a salt.

6. A composition according to claim 4, wherein said salt is a zinc salt.

7. A composition according to claim 1, wherein said fatty phase comprises at least one hydroxylated oil.

8. A composition according to claim 7, wherein said at least one hydroxylated oil represents from 0.2 to 99.95% of the total weight of the composition.

9. A composition according to claim 8, wherein said at least one hydroxylated oil represents from 1 to 80% of the total weight of the composition.

10. A composition according to claim 7, wherein said at least one hydroxylated oil is chosen from:
    liquid triglycerides;
    synthetic ester and ethers; and
    $C_{12}$ to $C_{26}$ fatty alcohols.

11. A composition according to claim 7, wherein said at least one hydroxylated oil is chosen from:
    castor oil,
    isostearyl lactate, octyl hydroxystearate, octyldodecyl hydroxystearate, diisostearyl malate, propylene glycol monoisostearate, polyglyceryl-3 diisostearate, and PPG-10 butanediol; and
    octyldodecanol, 2-hexyldecanol, 2-undecylpentadecanol and oleyl alcohol.

12. A composition according to claim 1, further comprising at least one non-hydroxylated oil chosen from:
    liquid triglycerides of linear or branched, saturated or unsaturated fatty acids of 4 to 10 carbon atoms, which are liquid at room temperature;
    synthetic esters and ethers;
    linear or branched hydrocarbons of synthetic or mineral origin; and
    linear or cyclic, volatile or non-volatile polydimethylsiloxanes which are liquid or pasty at room temperature, said polydimethylsiloxanes containing alkyl, alkoxy or phenyl groups, pendant or at the end of the silicone chain, said alkyl or alkoxy groups containing from 2 to 24 carbon atoms.

13. A composition according to claim 12, wherein said synthetic esters and ethers are fatty acids.

14. A composition according to claim 13, wherein said fatty acids are oils of formula $R_3COOR_4$ in which $R_3$ represents a $C_7$ to $C_{29}$ higher fatty acid residue and $R_4$ represents a $C_3$ to $C_{30}$ hydrocarbon-based chain.

15. A composition according to claim 1, further comprising at least one cosmetic and/or dermatological active agent other than acexamic acid.

16. A composition according to claim 15, wherein said at least one cosmetic and/or dermatological active agent is chosen from emollients, moisturizers, vitamins, lanolin, essential fatty acids, sunscreens titanium oxide and iron oxide.

17. A composition according to claim 1, further comprising at least one particulate filler.

18. A composition according to claim 1, wherein said composition is in the form of an oil-in-water or water-in-oil emulsion or in the form of a solid or supple, anhydrous composition.

19. A composition according to claim 1, further comprising at least one ingredient chosen from water, water-soluble or liposoluble dyes, antioxidants, essential oils, preserving agents, fragrances, gelling agents for an aqueous phase, neutralizing agents, liposoluble polymers, gelling agents for a liquid fatty phase, waxes, gums and surfactants.

20. A composition according to claim 1, wherein said composition is in the form of a lip balm or a lipstick or a lip gloss having treating properties.

21. A composition according to claim 1, wherein said composition is in the form of a stick.

22. A thickened anhydrous make-up composition for the lips, comprising a fatty phase containing acexamic acid as a physiologically acceptable active care agent and a thickener.

23. A composition according to claim 22, further comprising at least one hydroxylated oil, a silicone oil and/or a particulate filler.

24. A method of treating the human lips comprising the step of applying an effective amount of a composition according to claim 1 to said lips.

25. A method of treating the human lips comprising the step of applying an effective amount of a composition according to claim 22 to said lips.

26. A method of treating the human lips comprising applying an effective amount of acexamic acid to limit or prevent drying out of the lips.

27. A method of treating the human lips comprising applying an effective amount of acexamic acid to limit or prevent oedema of the lips.

28. A method of treating the human lips comprising applying an effective amount of acexamic acid to limit or prevent cracking of the lips.

29. A method of treating the human lips comprising applying an effective amount of acexamic acid to limit or prevent chapping of the lips.

30. A method of treating the human lips comprising applying an effective amount of acexamic acid to protect the lips against weather otherwise adversely affecting said lips.

* * * * *

UNITED STATES PATENT AND TRADEMARK OFFICE
CERTIFICATE OF CORRECTION

PATENT NO.    : 6,280,714 B1
DATED         : August 28, 2001
INVENTOR(S)   : Pascal Arnaud et al.

It is certified that error appears in the above-identified patent and that said Letters Patent is hereby corrected as shown below:

<u>Column 8, claim 11,</u>
Line 4, "octyidodecyl" should read -- octyldodecyl --.

Signed and Sealed this

Twelfth Day of March, 2002

Attest:

JAMES E. ROGAN
*Director of the United States Patent and Trademark Office*

*Attesting Officer*